United States Patent [19]

La Gro

[11] 4,274,848
[45] Jun. 23, 1981

[54] GAS-VENTING FILTER FOR COLLECTION APPLIANCE

[75] Inventor: Phillip A. La Gro, Des Plaines, Ill.

[73] Assignee: Hollister Incorporated, Chicago, Ill.

[21] Appl. No.: 78,514

[22] Filed: Sep. 24, 1979

[51] Int. Cl.³ .............................................. A61F 5/44
[52] U.S. Cl. ..................................... 55/387; 128/283
[58] Field of Search .......................... 55/387; 210/502; 128/283

[56] References Cited

U.S. PATENT DOCUMENTS

| | | | |
|---|---|---|---|
| 3,019,127 | 1/1962 | Czerwonka et al. | 210/502 X |
| 3,315,447 | 4/1967 | Meira | 55/387 X |
| 3,952,727 | 4/1976 | Nolan | 55/387 X |
| 3,960,771 | 6/1976 | Tanaka et al. | 210/502 |
| 4,160,059 | 7/1979 | Samejima | 55/387 |

Primary Examiner—John Adee
Attorney, Agent, or Firm—Tilton, Fallon, Lungmus

[57] ABSTRACT

An odor-adsorbing gas-venting filter assembly for a collection appliance, such as an ostomy pouch, which includes a fibrous heat-sealable filter pad containing activated carbon and having a gas-pervious liquid barrier heat sealed to one face thereof. The pad and the liquid barrier integrated with it are confined between two panels of heat-sealable material joined together along their borders. One of the panels is formed of impervious thermoplastic material, has at least one central opening, and is heat sealed to the barrier layer along a zone extending about such opening. The sealed borders of the panels are in turn heat sealed to the wall of the collection appliance about its vent aperture so that gas escaping from the appliance cannot by-pass the odor-adsorbing filter.

22 Claims, 7 Drawing Figures

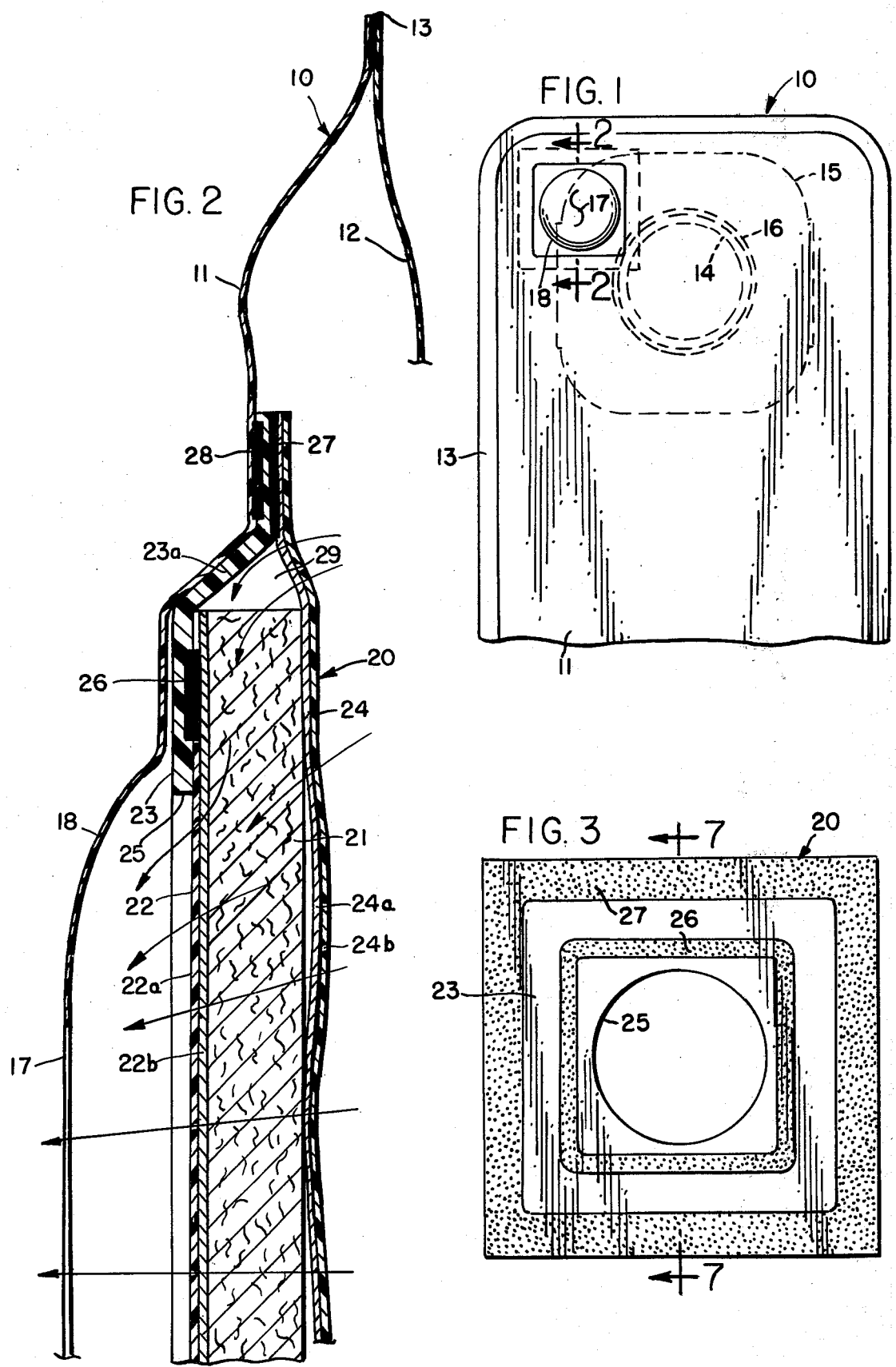

GAS-VENTING FILTER FOR COLLECTION APPLIANCE

BACKGROUND AND SUMMARY

Collection appliances such as colostomy and ileostomy pouches are vented to permit the escape of intestinal gases and prevent undesirable ballooning of such pouches in use. The vents are commonly provided with porous filter elements at the vent apertures for retaining liquid and/or solid matter within the pouches while selectively allowing the gases to escape. Ideally, such a filter also includes an adsorbent such as activated carbon to extract odors from the gases as they are vented. Although simple in general concept, such gas-venting filters are difficult to construct so that they operate consistently and effectively for the useful life of the appliance, a term ranging from several hours to a week or more depending on the nature of the surgical operation and the particular type of collection appliance involved. Thus, the filter assembly should resist clogging when exposed to solid matter, should be capable of withstanding moisture or even direct contact with liquids, should have sufficient odor-adsorbing capability, and should be constructed so that it cannot be by-passed by gases or, for that matter, by any of the contents of the appliance. In general, prior constructions have been only partially successful in meeting such objectives.

It is therefore an object of this invention to provide an improved gas-venting filter for collection appliances which is far more effective than prior known constructions in preventing the by-passing flow of intestinal gases, which controls or meters the flow of the vented gases so that solids discharged into the bag may pass into the bag's lower portion without encountering obstruction and without at the same time allowing such gases to produce undesirable ballooning of the bag, which resists clogging and the adherence of solid matter discharged into the bag, and which is highly effective in adsorbing odors from the gases as they are vented. A further object is to provide such an improved filter assembly which not only has superior performance characteristics but which also is easier to manufacture and fabricate than gas-venting filter assemblies in current use.

One aspect of this invention lies in the recognition that by-pass problems and other problems associated with gas-venting filters in ostomy appliances might be eliminated or greatly reduced by utilizing thermoplastic fibers in the fabrication of a filter pad, and then heat bonding a gas-pervious liquid barrier layer directly to the pad. Such barrier layer may thereafter be heat sealed directly to a liquid and gas impervious thermoplastic film along a heat seal zone extending about a central opening (or openings) in the film. The film is in turn heat sealed to the inside surface of the collection pouch about the vent aperture thereof with the result that the two concentric seals prevent by-passing of the filter by gases to be vented from the pouch, the non-pervious thermoplastic film performing the additional function of deflecting gases towards and through the adsorbent filter on their way to the vent aperture.

The liquid barrier bonded to the filter pad prevents liquids from entering the pad, and the interior of the pouch to which the filter assembly is secured, without significantly affecting the outflow of gases from the bag. Therefore, an ostomate may wear such a collection device in the shower without fear that water might contact the filter pad and destroy or at least reduce its effectiveness. Similarly, a protective panel which is gas-pervious but liquid-impervious (at least to the extent required for the particular appliance) may be secured by heat sealing to the portion of the thermoplastic film or panel extending beyond the periphery of the pad, thereby enclosing the pad between such panels. The breathable but water-resistant properties of the rear or inside panel protect the porous filter pad from becoming deactivated by liquid within the pouch and the non-adherent character of the polymeric material from which such panel is preferably formed prevents solid and liquid materials within the pouch from blocking the flow of gases through the adsorbent filter and out through the vent opening.

The porosity of the barrier layer and the rear or inside panel of the filter assembly is substantially greater than that of the filter pad itself with the result that the carbon-fiber matrix controls or meters the rate of flow of gas escaping through the vent of a pouch. The filter medium should be of a thickness and composition to provide a value of approximately 10 to 30 seconds when its resistance to the passage of air is measured in accordance with ASTM Test D726-58 (Method A) and, in the final product, the exposed area of the face of the filter pad should fall within the general range of 0.2 to 0.8 square inches.

Other objects, features, and advantages of the assembly will become apparent from the specification and drawings.

DRAWINGS

FIG. 1 is a front elevational view of an ostomy pouch equipped with the filter assembly of this invention, part of the lower portion of the pouch being broken away.

FIG. 2 is a greatly enlarged fragmentary sectional view of the filter assembly and pouch taken along line 2—2 of FIG. 1.

FIG. 3 is a front elevational view, enlarged to a lesser extent than the view of FIG. 2, of a filter assembly of this invention.

DETAILED DESCRIPTION

Figure 4:
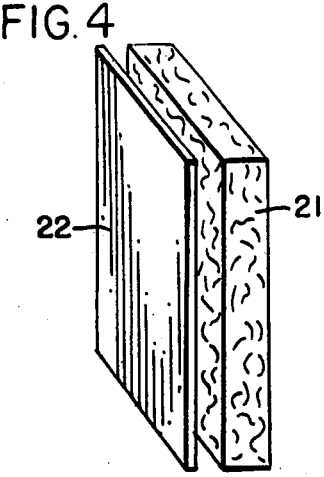
FIGS. 4–6 are schematic perspective views illustrating a sequence of steps in the fabrication of a filter assembly of this invention.

Referring to the drawings (FIGS. 1 and 2), the numeral 10 generally designates an ostomy pouch or bag having front and rear walls 11 and 12 formed of flexible fluid-impermeable thermoplastic sheet material. The front wall 11 and rear wall 12 are sealed around their peripheries by a heat-sealed bond 13 or by any other suitable means. The flexible walls may be formed of any effective gas and liquid impervious thermoplastic material such as, for example, a polyolefin film laminated with an appropriate barrier material. A particularly suitable commercial material comprises low density polyethylene coextruded with a coextensive layer or core of polyvinylidene chloride. Such material is commercially available under the designation "Saranex" from Dow Chemical Company, Midland, Michigan.

The rear panel 12 of the ostomy appliance 10, in accordance with standard practice, is provided with a stoma-receiving opening 14 (shown in dotted lines in FIG. 1). The outline of the adhesive attachment patch 15 is also depicted. In the illustration given, the patch 15 consists of a sheet of thermoplastic material which has an opening corresponding with opening 14 which is heat sealed as indicated at 16 to the outside of rear panel 12 around the opening 14. From the heat seal, the patch 15 extends outwardly in separated relation to the rear panel. The rear surface of the patch 15 may be coated with a pressure-sensitive medical adhesive so that, after removal of a protective backing sheet from the adhesive, the ostomy appliance may be adhered to the skin about the stoma. Such adhesive attachment provides a seal around the stoma so that solids, liquids, and/or gases discharged through the stoma will pass into the enclosure of the pouch.

Where the pouch has a substantial downward extent and is designed to retain appreciable amounts of discharge from the stoma, a relatively rigid gasket may be heat sealed to the rear panel of the pouch, being interposed between the adhesive patch 15 and the wall of the pouch around the stoma opening. The gasket may be provided with belt attachment tabs for additional support of the ostomy appliance, and a protective sealing composition may be applied to the gasket in the form of a ring, such as karaya, or mixtures of hydrocolloids with synthetic resins or elastomeric adhesives. It will be understood that patch 15 may be formed of breathable sheet material, such as a microporous non-woven sheet material. These details do not form a necessary part of the present invention and, since they are well known in the present commercial art of ostomy appliances, it is not believed necessary to describe them further herein.

The front wall 11 of the pouch is imperforate except for a vent aperture 17 located near the upper end of the pouch. In the embodiment illustrated, the vent is in the form of an S-shaped slit defining a pair of arcuate flaps which face in opposite directions, each flap serving as a flexible closure element which tends to be self-closing in the absence of a pressure differential. The slit extends generally vertically and is located in a bubble-like protrusion 18 formed in the flexible wall of the pouch. The structure and function of the bubble configuration, as well as the slit and associated closure flaps, are presented in detail in co-owned co-pending application Ser. No. 968,445, filed Dec. 11, 1978. Such features are shown here only to present the environment for a preferred embodiment of the present invention, it being understood that the filter assembly of this invention does not necessitate the bubble construction and that other shapes of apertures might be formed in wall 11 to vent gases flowing from the pouch through the filter assembly.

Figure 7:
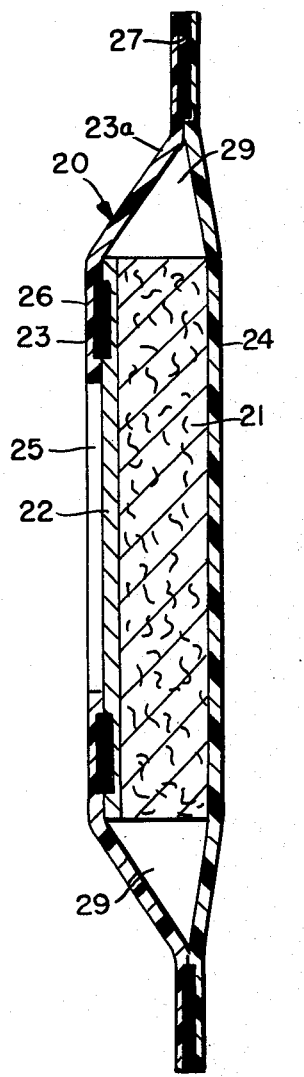
FIG. 7 is a cross sectional view of the completed filter assembly before it is secured to an ostomy appliance, such view being taken along line 7—7 of FIG. 3 and being simplified in certain respects for illustrative purposes.
Figure 7:
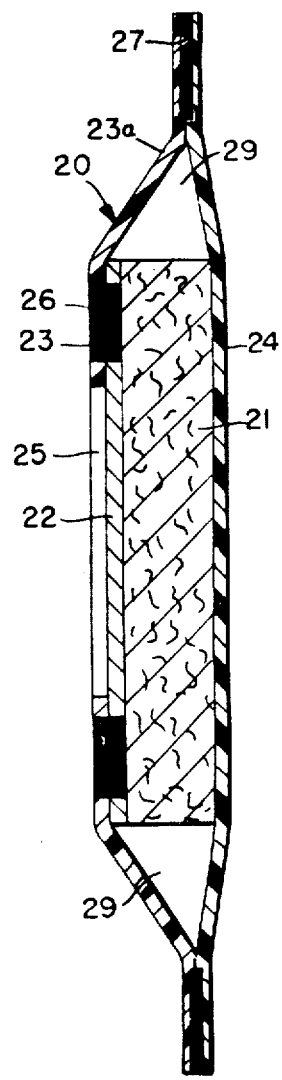

The filter assembly is designated generally by the numeral 20 and includes a porous filter pad 21, a gaspervious heat-sealable liquid barrier 22 secured by heat sealing to one face (the front or outer face) of the pad, a first flexible panel 23 of fluid-impermeable (i.e., both liquid and gas impermeable) thermoplastic material secured to the barrier layer 22 and projecting beyond the periphery of the pad 21, and a second flexible panel 24 extending over and beyond the opposite side of the pad, the two panels being sealed to each other about the periphery of the pad. The basic relationship of parts is depicted in FIG. 7 where, for clarity of illustration, certain of the panels or layers are shown as being of unitary non-laminated construction. While single-thickness layers and panels may indeed be used, it has been found advantageous to employ laminates to obtain the combined advantages of different materials. Therefore, for reasons described in detail hereinafter, some or all of the layers and panels may be laminated as shown in FIG. 2, such figure depicting in somewhat schematic form what is believed to be a particularly effective commercial embodiment of the invention.

Filter pad 21 is composed predominately of thermoplastic fibers coated with finely-divided activated carbon and secured together by a suitable binder to provide a porous odor-adsorbing filter matrix. Because the fibers of the pad are thermoplastic, the pad may be heat sealed to other compatible thermoplastic materials. Such heat sealability of the pad plays an important role in achieving a filter assembly which is readily fabricated and secured to the wall of an ostomy pouch or bag, and which cannot be by-passed when so fabricated, assembled, and used in the manner intended.

The filter pad 21 may be manufactured using standard paper-making techniques but with suitable thermoplastic fibers substituted for natural cellulosic fibers. A fibrillated polyethylene fiber marketed under the designation "SWP" synthetic pulp by Crown Zellerbach, Camas, Washington, has been found particularly effective although other thermoplastic fibers having similar properties might be used. Such fibers should be relatively short, the majority having a length falling within the range of about 1 to 4 millimeters. A preferred length is believed to be about 2 millimeters. If desired, such fibers may be blended with a limited amount (no greater than about 15%) natural fibers to impart greater strength to the final product.

The fibers of the filter pad are coated with finely-divided activated carbon using a suitable binder such as a conventional latex binder used in paper-making procedures. A high grade of activated carbon should be used for best results. Type IVP activated carbon, or type RB activated carbon, as supplied by Calgon Corporation, Pittsburgh, Pennsylvania, may be used. The carbon should be finely-divided with the maximum size thereof being no greater than 100 microns and with a size distribution in which more than one half of the particles are less than 50 microns in size. Approximately equal amounts by weight of the thermoplastic fiber and activated carbon may be used. With a 50% impregnation or coating ratio, it has been found that filter pad 21 may perform effectively as a deodorizing element for vented gases even though its thickness is as small as 1 to 1.5 mm.

The filter pad 21 should be capable of metering or controlling the flow of discharged gas at a predetermined rate. If gas is discharged too rapidly from the pouch, then when the filter assembly is utilized in a colostomy appliance there is a possibility that the venting will be too fast to allow fecal matter to clear the area near the stoma and drop to the lower portion of the bag. On the other hand, if the flow rate of vented gases is too slow, undesirable ballooning of the collection device may occur. In general, the filter should be dimensioned and fabricated so that the flow therethrough, measured in terms of seconds required to allow the passage of 100 cc of air per square inch at a pressure equal to 4.9 in. (124 mm) of water, in accordance with Method A of ASTM test D726-58 (1971), will fall within the range of about 10 to 30 seconds. A filter pad meeting those requirements may be made utilizing fibrillated polyethylene fibers providing 8 to 12 square meters of surface area per gram of fiber material and a fiber length of approximately 1 to 4 mm, combined with approximately equal amount by weight of activated carbon as already described, along with a suitable latex binder, to form a paper (utilizing standard paper-making procedures) having a thickness of approximately 1 to 2.5 mm. The planar area of such a filter exposed to gas flow should fall within the range of about 0.2 to 0.8 in.$^2$ or approximately 1.3 to 5.2 cm$^2$. It is to be understood, however, that there may be considerable variation in the dimensions and proportions of the components while still achieving flow rates within the range of 10 to 30 seconds per 100 cc air under the ASTM standard mentioned above, and that such dimensions and proportions are set forth for illustrative purposes only.

The barrier layer 22 extending over the front or outer face of the filter pad 21 may be formed of any breathable and heat sealable material which is resistant to water penetration. Although the porous barrier layer will necessarily present some resistance to the passage of gas, that resistance must in any case be less than the resistance presented by the filter pad itself, the result being that only the filter medium serves as the metering element in controlling the rate of flow of gas from the collection appliance.

The liquid barrier layer 22 should also be relatively strong, serving as a reinforcement for the weaker filter pad 21, and should present an outer or front surface resistant to soiling and particulate accumulation. While a number of materials might have the desired combination of properties, effective results have been obtained using a reinforced non-woven cellulosic material sold under the trademark "Kaycel" by Kimberly-Clark Corporation, Neenah, Wisconsin. Such material is not only air-pervious; it is also surface coated by an ethyl vinyl acetate latex emulsion so that it is both water resistant and heat sealable. Its strength and durability provide substantial reinforcement for the filter pad 21 heat sealed directly to the barrier layer. While the Kaycel tends to resist soiling and the accumulation of particulate matter, such resistance may be increased by including a porous thermoplastic film as part of the barrier layer. A porous expanded high-density polyethylene or polypropylene film of the type marketed under the designation "Delnet" by Hercules Incorporated, Wilmington, Delaware, has been found effective but other porous thermoplastic films or membranes such as "Gore-tex", a microporous polytetrafluoroethylene membrane marketed by W. L. Gore & Associates, Newark, Delaware, may be employed. In FIG. 2, the outer soil-resistant component is designated by numeral 22a and the inner heat-sealable component of the barrier layer is represented by numeral 22b. As already indicated, the heat-sealable gas-transmitting liquid barrier layer 22 may be composed of a lesser or greater number of plies depending on the amount of water resistance, tensile strength, soil resistance, and other properties, believed necessary or desirable. Since, regardless of the number of plies, the barrier layer 22 represents a single element that functions to reinforce the filter pad, block the entry of liquid, allow the escape of gas, and provide heat sealability, such liquid barrier layer is represented only as a single component in FIGS. 4–7.

Panel 23 is formed of any suitable thermoplastic film (or film laminate) which is capable of being heat sealed to both the barrier layer 22 and to wall 11 of a collection appliance, and is also impervious to body liquids and gases. "Saranex," already identified, has been found particularly effective, but other thermoplastics having similar properties may be used. As shown most clearly in FIGS. 2, 3, 6, and 7, layer 23 has an outer portion 23a extending beyond the periphery of pad 21, and also has at least one central aperture 25 exposing a substantial portion of the surface of the filter pad/barrier layer combination which, in terms of assembly, may be regarded as the filter unit. A heat-sealed zone 26 extends continuously about opening 25 and joins panel 23 and barrier layer 22 against the passage of gases (or liquids) in any radial directions (i.e., in directions radiating outwardly from opening 25) between their opposing surfaces.

The second panel 24 may, like liquid barrier layer 22, be formed of one or more plies of a reinforcing, liquid-resistant, gas-transmitting, heat-sealable material. A non-woven cellulosic material such as Kaycel, surface treated to impart heat sealability and water resistance, may be effectively used. In FIG. 2, such a non-woven material is one of the plies 24a of a two-ply laminate, the outer ply 24b being formed of Delnet. Thus, the composition of panel 24 may be the same as that of barrier layer 22 although, as indicated in FIG. 2, the inner panel 24 need not be heat sealed, and is preferably not so sealed, to filter pad 21.

The water resistance of a treated non-woven cellulosic material, although sufficient to prevent liquid transmission through the filter assembly for many ostomy appliances such as, for example, a colostomy bag, may be insufficient for other applications where greater amounts of liquid would normally be collected, as in an ileostomy appliance. In the latter case, it may be desirable to substitute the non-woven cellulosic material of panel 24 (and even that of barrier layer 22) with a gas-pervious sheet material having greater resistance to water transmission. Thus, the microporous polytetrafluoroethylene marketed under the Gore-tex trademark may be substituted for the non-woven cellulosic material, or other microporous thermoplastic materials having properties similar to such polytetrafluoroethylene may be used. Where panel 24 is to be a laminate of Gore-tex and some other material such as, for example, Delnet, such laminate is preferably oriented so that the Gore-tex is exposed to the inside of the collection bag or pouch 10 because of the greater resistance of the fluorinated hydrocarbon polymer to soiling and the adherence of particulate matter.

Figure 5:
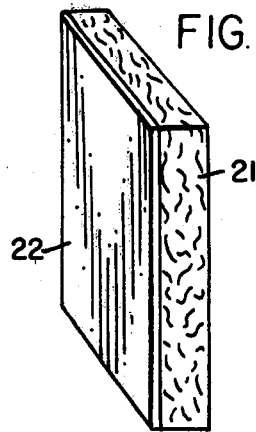
Figure 6:
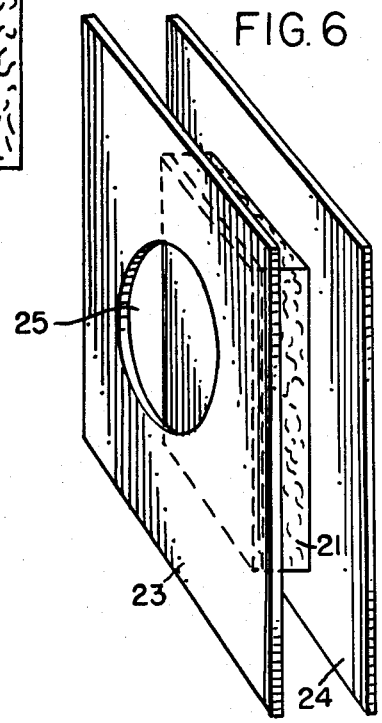

Certain steps in the fabrication of the filter assembly are depicted in FIGS. 4 through 7. The filter unit, composed of filter pad 21 and liquid barrier layer 22, is first prefabricated by heat sealing the opposing surfaces of such elements together as indicated in FIGS. 4 and 5. Thereafter, the outer portions of the heat-sealable panels 23 and 24 are sealed together along primary seal zone 27 to enclose or sandwich the filter unit therebetween. At the same time, the secondary heat seal 26 is formed between front panel 23 and the liquid barrier 22. Each of the heat seal zones 26 and 27 is continuous or unbroken, with the result that gas entering the rear of the filter assembly through panel 24 must pass through the filter if such gas is to exit through opening 25 in panel 23.

The filter assembly shown in FIGS. 3 and 7 is a preassembled unit which may be secured within any of a variety of collection appliances. FIGS. 1 and 2 illustrate the filter assembly secured within an ostomy pouch 10 by means of a final heat seal 28 which extends along, and may be fused with and become a part of, primary seal 27. The two seals are shown separately in FIG. 2 only for clarity of illustration. Seal 28 prevents external by-passing of the filter assembly 20—that is, prevents gases (or liquids) from escaping pouch 10 by passing between front panel 23 and front wall 11. The secondary seal 26 prevents by-passing internally of the filter assembly; in other words, prevents gases which enter the triangular-shaped space 29 shown in FIG. 2 from reaching opening 25 by any route other than through filter 21.

While in the foregoing I have disclosed an embodiment of the invention in considerable detail for purposes of illustration, it will be understood by those skilled in the art that many of these details may be varied without departing from the spirit and scope of the invention.

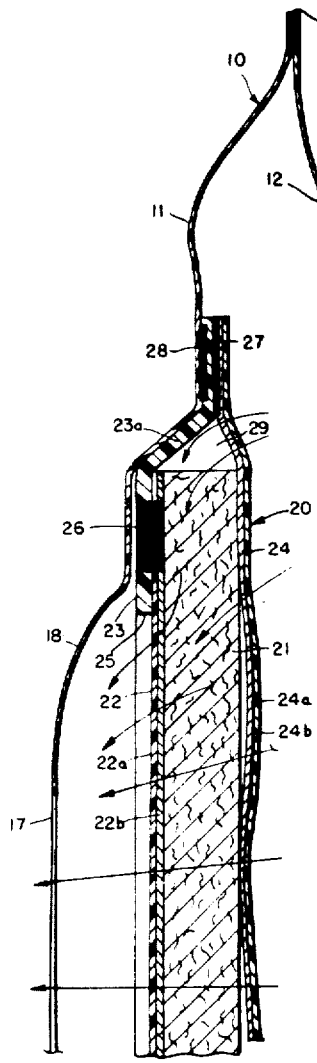

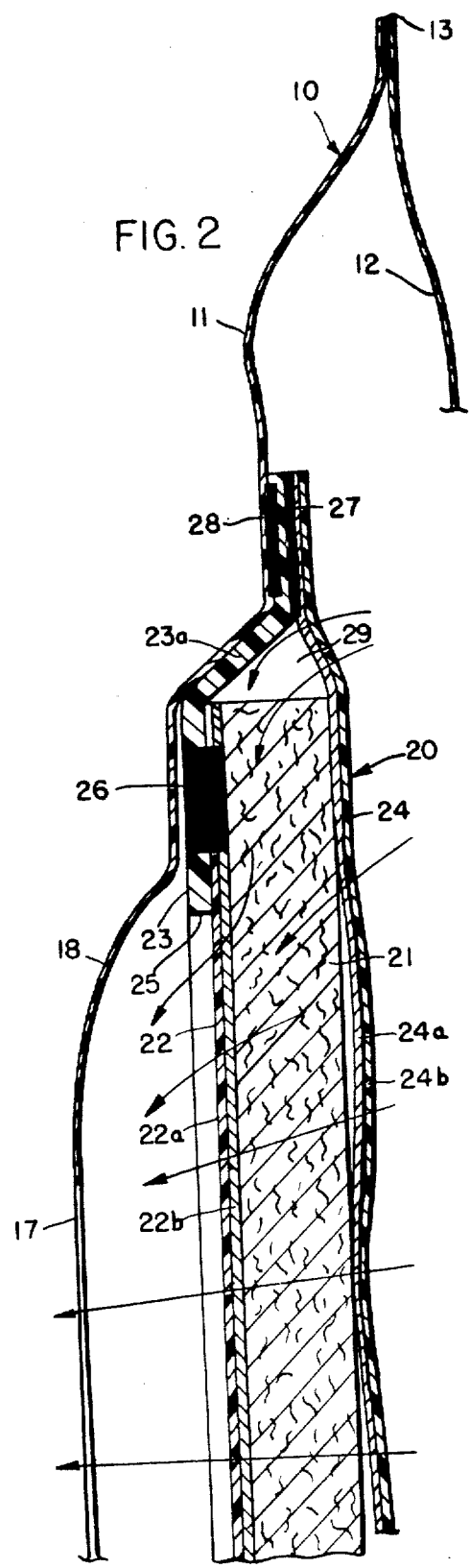

I claim:

1. An odor-adsorbing gas filter assembly for use in collection appliances, comprising a porous filter pad having a pair of opposite planar faces and comprising a network of thermoplastic fibers coated with finely-divided activated carbon, a heat-sealable gas-pervious liquid barrier secured to one of said faces, a first panel of gas-impermeable thermoplastic material extending over said barrier and including a border portion projecting beyond the periphery of said pad, said panel having at least one central opening therethrough for the escape of gas flowing through said filter pad and being heat sealed to said barrier along a heat-seal zone extending uninterruptedly about said opening, said barrier being sealed by said heat seal against the transmission of gas through said zone, whereby, gas passing through said opening from the direction of said filter pad cannot by-pass said pad, and a second panel of porous material extending over the face of said pad opposite from said barrier and having a border portion projecting beyond the periphery of said pad, said border portions of said panels being sealed together to enclose said pad between said panels.

2. The assembly of claim 1 in which said second panel is formed of heat-sealable material and said border portions of the respective panels are heat sealed together.

3. The assembly of claim 1 in which the majority of fibers of said pad are of lengths falling within the range of 1 to 4 millimeters.

4. The assembly of claim 1 in which said pad has an air transmission value within the range of about 10 to 30 seconds per 100 cubic centimeters of air when measured in accordance with ASTM D726-58, Method A.

5. The assembly of claims 1, 2, 3, or 4 in which said fibers of said pad are formed of fibrillated polyethylene.

6. The assembly of claim 1 in which said activated carbon is composed of particles more than half of which are smaller than 50 microns in size.

7. The assembly of claim 6 in which said activated carbon particles are adhesively secured to said thermoplastic fibers.

8. The assembly of claim 1 in which said gas-pervious liquid barrier is a laminate comprising a porous thermoplastic layer bonded to a heat-sealable fibrous layer.

9. The assembly of claim 1 in which said filter pad has an air transmission value within the range of about 10 to 30 seconds per 100 cubic centimeters of air when measured in accordance with ASTM D726-58, Method A, said gas-pervious liquid barrier and said second panel each having an air transmission value substantially greater than that of said filter pad.

10. The assembly of claim 1 in which said second panel comprises microporous polytetrafluoroethylene.

11. The assembly of claim 1 in which said second panel comprises non-woven cellulosic fibers having a thermoplastic coating thereon.

12. The assembly of claims 10 or 11 in which said second panel also includes a porous film of high-density polyethylene laminated thereto.

13. An ostomy appliance having thermoplastic walls joined at their periphery to define a pouch and being provided with a stoma-receiving opening, one of said walls having a vent opening for the venting of gases from said pouch, and an odor-adsorbing gas filter assembly secured to said one wall at said vent opening, said assembly comprising a porous filter pad having a pair of opposite planar faces and comprising a network of thermoplastic fibers coated with finely-divided activated carbon, a heat-sealable gas-pervious liquid barrier secured to one of said faces, a first panel of gas-impermeable thermoplastic material extending over said barrier and including a border portion projecting beyond the periphery of said pad, said panel having at least one central opening therethrough for the escape of gas and being heat sealed to said barrier along a heat-seal zone extending uninterruptedly about said opening, said barrier being sealed by said heat seal against the transmission of gas through said zone, whereby, gas passing through said opening from the direction of said filter pad cannot by-pass said pad, a second panel of porous thermoplastic material extending over the face of said pad opposite from said barrier and having a border portion projecting beyond the periphery of said pad, said border portions of said panels being heat sealed to each other and to said one wall of said pouch about said vent opening along a second heat-seal zone extending uninterruptedly about said pad to enclose said pad between said panels and to secure said assembly to said pouch.

14. The appliance of claim 13 in which said fibers of said pad are formed of fibrillated polyethylene of lengths falling within the range of 1 to 4 millimeters.

15. The appliance of claim 13 in which said activated carbon is composed of particles more than half of which are smaller than 50 microns in size.

16. The appliance of claim 15 in which said activated carbon particles are adhesively secured to said thermoplastic fibers.

17. The appliance of claim 13 in which said filter pad has an air transmission value within the range of about 10 to 30 seconds per 100 cubic centimeters of air when measured in accordance with ASTM D726-58, Method A, said gas-pervious liquid barrier and said second panel each having an air transmission value substantially greater than that of said filter pad.

18. The appliance of claim 13 in which said second panel comprises microporous polytetrafluoroethylene.

19. The appliance of claim 13 in which said second panel comprises non-woven cellulosic fibers having a thermoplastic coating thereon.

20. The appliance of claims 18 or 19 in which said second panel also includes a porous film of high-density polyethylene laminated thereto.

21. A non-bypassing odor-adsorbing gas filter assembly suitable for use in collection appliances, comprising a porous filter containing activated carbon and having a pair of opposite planar faces, at least one of said faces of said filter being heat sealable; a first panel of gas-impermeable thermoplastic material extending over said one of said faces and including a border portion projecting beyond the periphery of said filter; said panel having at least one central opening therethrough for the escape of gas flowing through said filter and being heat sealed to said filter along a heat-seal zone extending uninterruptedly about said opening, whereby, gas passing through said opening from the direction of said filter cannot by-pass said filter; and a second panel of porous material extending over the face of said filter opposite from said one face and having a border portion projecting beyond the periphery of said filter; said border portions of said panels being sealed together to enclose said pad between said panels.

22. A non-bypassing odor-adsorbing gas filter assembly suitable for use in collection appliances, comprising a porous filter containing activated carbons and having a pair of opposite planar faces, at least one of said faces of said filter being heat sealable; a panel of gas-impermeable thermoplastic material extending over said one of said faces and including a border portion projecting beyond the periphery of said filter; said panel having at least one central opening therethrough for the escape of gas flowing through said filter and being heat sealed to said filter along a heat-seal zone extending uninterruptedly about said opening, whereby, gas passing through said opening from the direction of said filter cannot by-pass said filter.

* * * * *

UNITED STATES PATENT AND TRADEMARK OFFICE
CERTIFICATE OF CORRECTION

PATENT NO. : 4,274,848　　　　　　　　　　　　Page 1 of 4

DATED : June 23, 1981

INVENTOR(S) : Phillip A. La Gro

It is certified that error appears in the above—identified patent and that said Letters Patent is hereby corrected as shown below:

The title page and the descriptive figure should appear as shown on the attached sheet.

Figures 2 and 7 should appear as shown on the attached sheets.

Signed and Sealed this

Eleventh Day of May 1982

[SEAL]

Attest:

Attesting Officer

GERALD J. MOSSINGHOFF

Commissioner of Patents and Trademarks

United States Patent [19]

La Gro

[11] 4,274,848
[45] Jun. 23, 1981

[54] GAS-VENTING FILTER FOR COLLECTION APPLIANCE

[75] Inventor: Phillip A. La Gro, Des Plaines, Ill.

[73] Assignee: Hollister Incorporated, Chicago, Ill.

[21] Appl. No.: 78,514

[22] Filed: Sep. 24, 1979

[51] Int. Cl.³ .................................................... A61F 5/44
[52] U.S. Cl. ..................................... 55/387; 128/283
[58] Field of Search ........................ 55/387; 210/502; 128/283

[56] References Cited

U.S. PATENT DOCUMENTS

| | | | |
|---|---|---|---|
| 3,019,127 | 1/1962 | Czerwonka et al. | 210/502 X |
| 3,315,447 | 4/1967 | Meira | 55/387 X |
| 3,952,727 | 4/1976 | Nolan | 55/387 X |
| 3,960,771 | 6/1976 | Tanaka et al. | 210/502 |
| 4,160,059 | 7/1979 | Samejima | 55/387 |

Primary Examiner—John Adee
Attorney, Agent, or Firm—Tilton, Fallon, Lungmus

[57] ABSTRACT

An odor-adsorbing gas-venting filter assembly for a collection appliance, such as an ostomy pouch, which includes a fibrous heat-sealable filter pad containing activated carbon and having a gas-pervious liquid barrier heat sealed to one face thereof. The pad and the liquid barrier integrated with it are confined between two panels of heat-sealable material joined together along their borders. One of the panels is formed of impervious thermoplastic material, has at least one central opening, and is heat sealed to the barrier layer along a zone extending about such opening. The sealed borders of the panels are in turn heat sealed to the wall of the collection appliance about its vent aperture so that gas escaping from the appliance cannot by-pass the odor-adsorbing filter.

22 Claims, 7 Drawing Figures